United States Patent [19]

Hoffmann

[11] Patent Number: 5,176,915
[45] Date of Patent: Jan. 5, 1993

[54] PLASTER USED AS THERAPEUTIC SYSTEM FOR THE ADMINISTRATION OF ACTIVE SUBSTANCES TO THE SKIN WHICH EXHIBITS A GRADUATED ACTIVE SUBSTANCE RELEASE, PROCESS FOR THE PRODUCTION OF THE PLASTER AND THE USE THEREOF

[75] Inventor: Annegrete Hoffmann, Neuwied, Fed. Rep. of Germany

[73] Assignee: LTS Lohmann, Neuwied, Fed. Rep. of Germany

[21] Appl. No.: 721,903

[22] Filed: Jun. 20, 1991

Related U.S. Application Data

[63] Continuation of Ser. No. 492.523, Mar. 12, 1990, abandoned.

[30] Foreign Application Priority Data

Mar. 15, 1989 [DE] Fed. Rep. of Germany ....... 3908432

[51] Int. Cl.⁵ ............................................. A61L 15/00
[52] U.S. Cl. ................................... 424/445; 424/443; 424/444; 424/446; 424/447; 424/448; 424/449
[58] Field of Search .............. 424/443, 444, 445, 446, 424/447, 448, 449

[56] References Cited

U.S. PATENT DOCUMENTS

| | | | |
|---|---|---|---|
| 3,731,683 | 5/1973 | Zaffaroni | 128/268 |
| 4,597,961 | 7/1986 | Etscorn | 424/48 |
| 4,666,441 | 5/1987 | Andriola | 604/897 |
| 4,698,062 | 10/1987 | Gale | 604/896 |

Primary Examiner—Thurman K. Page
Assistant Examiner—D. Gabrielle Phelan
Attorney, Agent, or Firm—Sprung, Horn, Kramer & Woods

[57] ABSTRACT

The present invention relates to a plaster used as therapeutic system for the administration of active substances to the skin exhibiting an graduated active substance release, to the process for the production of such a plaster, and to the use for the local or systemic dermal adminstration of active substances in the human or veterinary medicine, or in cosmetics.

14 Claims, 2 Drawing Sheets

PLASTER USED AS THERAPEUTIC SYSTEM FOR THE ADMINISTRATION OF ACTIVE SUBSTANCES TO THE SKIN WHICH EXHIBITS A GRADUATED ACTIVE SUBSTANCE RELEASE, PROCESS FOR THE PRODUCTION OF THE PLASTER AND THE USE THEREOF this application is a continuation of application Ser. No. 492,523, filed Mar. 12, 1990, abandoned.

DESCRIPTION

The present invention relates to a plaster used as therapeutic system for the administration of active substances to the skin, said plaster exhibiting graduated active substance release, to the process for the production of such a therapeutic system, and to its use for the local or systemic dermal administration of active substances in the human or veterinary medicine, or in cosmetics.

Therapeutic devices for the controlled administration of drugs are called therapeutic systems (K. Heilmann, Therapeutische Systeme, page 26, publishers F. Enke, Stuttgart, 1984). According to this publication such a system is an active substance containing device or form of administration, respectively, which continuously releases one or more pharmaceuticals at a predetermined rate over a fixed period of time to a fixed place of application.

Such systems may have topical as well as a systemic effects when applied to the skin, and the variety of active substances applicable by way of these systems and the different chemical, physical, and pharmacological properties of the drugs always demand for new requirements in the production of such systems. For example, in the case of dermal application, solutions for many active substances have been found in which a continuous, substantially constant release over the desired period of application has been achieved.

However, there are also therapeutical requirements according to which the release profile of the drug has to exhibit a high initial dosage followed by a lower maintenance dosage. For example, in case of soporifics, high delivery of active substance for sleep induction, and a lower dosage to prevent awakening over a longer period of time after sleep induction is desired. In the case of appetite-suppressing agents, too, higher blood levels of active substance shall be adjustable during the day compared to those during the night. The same applies to the administration of nicotine in the curing of smokers. Not least the treatment of pain attacks is mentioned, where after a high initial dosage a lower maintenance dosage is desirable.

A transdermal therapeutic system to solve this problem has been described in EP-A 0 227 252. In this case, the active substance in a reservoir is brought into contact with an amount of penetration accelerator merely sufficient to maintain the accelerated penetration only during a defined initial phase of application. It is of disadvantage in this case that each active substance has to assigned a suitable penetration accelerator, and that in the choice of the reservoir matrix in addition to considering the diffusivity of the active substance that of the penetration accelerator has to be taken into consideration, too. In the latter case, an expensive additional controlling membrane is frequently required.

Another solution to this problem has been proposed in DE-OS 36 42 931. In this case, at least two plaster chambers being separate from each other are provided with different active substance concentrations so that in the first application phase the release of active substance from all chambers effects a high initial dosage, while after evacuation of the chambers with low active substance concentration only those chambers with higher active substance concentration contribute to the release, and thus effect a lowered maintenance dosage. This system is expensive merely because of this chamber construction, and requires special measures with respect to the different concentration adjustments in the chambers.

It is accordingly the object of the present invention to provide a plaster as therapeutic system with graduated drug release for the administration of active substances to the skin, which avoids the compelling presence of a penetration accelerator and can be manufactured in a simple manner.

According to the present invention, this object is surprisingly achieved by a plaster with a high initial dosage and a lower maintenance dosage, which is provided with a backing layer averted from the skin, at least one active substance deposit contacting a matrix, which controls the active substance release, and a pressure-sensitive adhesive fixing device for securing the plaster to the skin. In this connection, the whole matrix contains active substances at the time of application, and the dimension of the active substance containing deposit or deposits compared to that of the matrix, as well as the position of the active substance deposit or deposits in contact with the matrix are chosen is such a way that, at least in one direction, the space between deposit and edge of matrix, which contacts the releasing surface, is larger than the diffusion path of at least one active substance from the deposit into the matrix during the period of application.

Thus the subject matter of the present invention is a plaster used as therapeutic system for the controlled and graduated administration of active substances to the skin, with a high initial dosage and lower maintenance dosage comprising a backing layer averted from the skin, at least one active substance deposit in contact with a matrix controlling the active substance release, and a pressure-sensitive adhesive fixing device to secure the plaster to the skin, whereby the complete matrix at the beginning of the application comprises active substances, wherein the dimension and position of the active substance deposit or deposits in contact with the matrix are chosen in such a way that, at least in one direction, the space between deposit and a matrix edge, which contacts the releasing surface, is larger than the diffusion path from the deposit into the matrix during the course of application of at least one active substance.

The general design of the plaster according to the present invention is known from DE-OS 21 35 533, however, without having recognized the constructional features of the intended change in release profile according to the present invention.

An important feature of the plaster according to the present invention is that the matrix comprises active substance at the time of application. This can be achieved by two methods. On the one hand, the matrix may be loaded with active substances already during the manufacture of the plaster, or, on the other hand, the matrix is loaded with active substance after production of the plaster by diffusion of active substance from the active substance deposit into the matrix which up to then had been empty. The last mentioned process can be accelerated by temperature increase, and may last for hours or days. Thus, during the initial phase of application, active substance may issue over the whole releasing surface of the matrix (corresponds to high initial dosage) which results in a depletion of active substance in the bordering layers. This depletion can only be compensated by additional delivery of active substances from the active substance deposit. If the space between deposit and emptying zones is so large that it cannot be overcome during application due to the diffusitivity of the active substance, the active substance release comes to a standstill in these regions. Only those portions of the releasing surface of the matrix are still releasing active substances, which can be delivered by subsequent diffusion from the deposit (corresponding to a lower maintenance dosage). Thus, the geometric relations within the plaster are mainly determined by the desired release profile, the active substance to be administered, the choice of matrix, as well as the dimension and position of the deposit.

The active substance deposit containing one or more active substances may consist of pure active substance which may solid or flowable, however, said deposit may also contain inert auxiliaries. The term "inert" is to be understood in this connection in that the active substance and the auxiliary agent do not react with one another. Inert auxiliaries known to those skilled in the art, e.g., are solvents, fillers, stabilizers, supporting materials, carriers, and optionally as well additives regulating diffusion and penetration.

All transdermally applicable active substances for the application of which high initial dosages are indicated can be used as active substances. Active substances selected from the group consisting of analgesics, antiemetics, antiadipogenics, antiphlogistics, antispasmolytics, and antiangina-agents, are mentioned as examples. Nicotine employed as active substance for curing smokers does also belong to this group.

Advantageously the sum of active substances in the deposit and the matrix amounts to up to 20 times the therapeutically required amount.

The matrix is preferably built up in layers and/or as a laminate, whereby the layers can be the same or different. The matrix may be pressure-sensitive adhesive, this can be achieved by the use of adequate polymeric materials, e.g., rubber, rubber-like synthetic homo-, co-, or blockpolymers, poly(meth)acrylates and their copolymers, polyurethanes, and silicones. In principle, all polymers are suitable which are employed in the manufacture of pressure-sensitive adhesives and are physiologically acceptable. It may be advantageous, if the matrix is pressure-sensitive adhesive, since the necessity for a separate pressure-sensitive adhesive fixing device can be omitted. In case of a matrix not being pressure-sensitive adhesive, suitable polymeric materials are used, e.g., those selected from the group consisting of poly(meth)acrylates, polyvinylpyrrolidones, ethylcellulose, hydroxypropylcelluloses, hydroxypropylmethylcellulosephthalates, polyvinyl alcohols or their copolymers with vinyl laurate or maleic acid, respectively, vinyl acetates or their copolymers with vinyl laurate or maleic acid, respectively, polyvinyl ether, butyl rubbers, and polycaprolactames.

The active substance deposit may be composed of a single layer and/or of multiple layers in itself. The form of a layer of the active substance deposit is always preferred from the production standpoint, in cases where it can be achieved to adjust the active substance concentration in the layer in correspondence with the requirements and to maintain the necessary space to the matrix edge. The laminated construction of the substance deposit is preferred, if a direct mixture of drug-containing deposit portions with required or desired inert auxiliaries is impossible, or if advantages with respect to its production result; in this connection the deposit itself need not be in the form of a laminate.

In the construction of the plaster, for example, at least one active substance deposit may be inserted between a back side matrix layer and a matrix layer on the skin side, whereby the thickness ratio of the matrix layers preferably is in the range of 1:1 to 1:20, particularly preferred in the range of 1:1 to 1:5.

In another advantageous embodiment of the plaster according to the present invention, the active substance deposit may be located between matrix and backing layer, this is particularly suitable in case of solid active substance deposits which are applicable in the form of matter.

If the matrix is not self-adhesive, a pressure-sensitive adhesive layer may be provided for on that surface of the device facing the skin. In this case, the inner coherence of the device can also be managed by additional pressure-sensitive adhesive intermediate layers. According to a preferred embodiment of the present invention the fixing device may be built by pressure-sensitive adhesive sections embedded in the matrix, or by pressure-sensitive adhesive edges surrounding the releasing surface. The pressure-sensitive adhesive layers may also contain active substances thus contributing to the increase of the initial dosage.

The backing layer serves for the protection and/or mechanical stabilization of the device. It may consist of flexible or inflexible material and may be single or multilayered.

Substances suitable for its production are polymeric substances, such as, e.g., polyethylene, polypropylene, polyester, and polyamides. As further materials metal foils, e.g., an aluminum foil alone or coated with a polymeric substrate, may be used, too. Textile fabrics may also be used, if they are able to prevent the components of the device from escaping. Polymer foils vaporized with metal have proved particularly successful.

It is possible in a usual manner to provide for a removable protective layer on those surfaces of the plaster facing the skin, this protective layer prevents an undesirable contamination and premature release of the plaster components. This layer is removed only immediately prior to application. In principle, the same materials as used for the backing layer may be used for the manufacture of the protective layer, provided that they are removable, e.g., by way of a silicone treatment. Other removable protective layers, for example, are polytetrafluoroethylene, treated paper, cellophane, and polyvinyl chloride. As a matter of fact, the protective layer may be provided with a touch aid in order to facilitate stripping it off the plaster.

A preferred process for the production of the plaster according to the present invention is the in situ-production of the active substance deposit. In this connection, the deposit is built of the deposit components directly at the contact point to the matrix. As for the rest, the layers of the device are joined by applying pressure and/or heat. The deposit may also be integrated into the matrix by pressure, for example, by injection of a predetermined amount, or by pressing a deposit body into a soft matrix. According to a preferred process of the present invention, the active substance deposit is incorporated between two matrix layers which can be the same or different.

Advantageously at least one part of the plaster is produced of a solution, a dispersion, a melt, or by sprinkling particles. The areal intermediate products thus obtained are distributed to smaller units, the dimension and shape of which are determined by the therapeutical requirements.

The plaster according to the present invention is particularly suitable for the local and systemic dermal administration of active substances in the human or veterinary medicine, and can be used in cosmetics, too.

BRIEF DESCRIPTION OF THE DRAWINGS

In the following, the present invention shall be illustrated but not limited by the figures which, amongst others, show the schematic, not true to scale construction of the plasters according to the present invention:

FIG. 1a represents the schematic section through a plaster according to the prior art, in which an active substance deposit (13) is embedded in a pressure-sensitive adhesive matrix (12) which is covered by a backing layer (11). The space of the active substance deposit (13) from the edge of matrix (14) is so small that those regions of the matrix which are emptying during application can be refilled with active substance by diffusion. Thus active substance is released over the complete releasing surface during the whole period of application.

FIG. 1b shows the in vivo-release profile corresponding to this plaster, whereby the flux is indicated versus time. It can be seen that after achieving the maximum the flux mainly remains at the same level without gradation, for the rest of the time. Thus, according to this prior art, a substantially constant flux is maintained during the desired period of time.

Figure 1A:
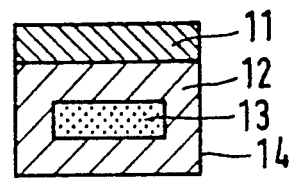
FIG. 1a shows a section through a plaster according to the prior art.
Figure 1B:
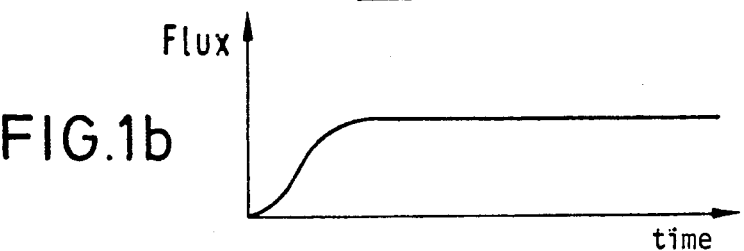
FIG. 1b shows a diagram of the in vivo-release profile of the plaster according to FIG. 1a, FIG. 2a shows a section through an embodiment of the plaster according to the present invention.
Figure 2A:
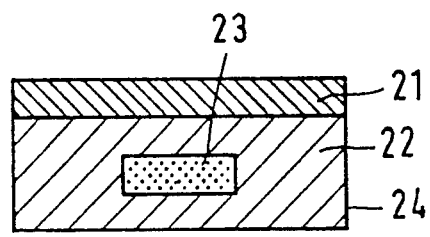
FIG. 2b shows a diagram of the in vivo-release profile of the plaster according to FIG. 2a, FIG. 3a shows a section through a further embodiment of the plaster according to the present invention.
Figure 2B:
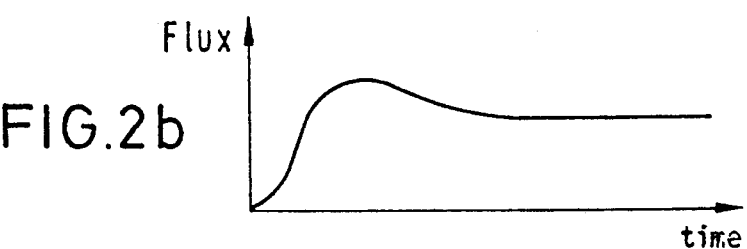

The schematic section through an embodiment of the plaster according to the present invention with backing layer (21), pressure-sensitive adhesive matrix (22), embedded deposit (23), and edge of matrix (24) as shown in FIG. 2a shows a considerably extended space between deposit (23) and edge of matrix (24) compared to that of the plaster according to FIG. 1a. If the matrix (22) is correctly adapted to the individual active substance, the active substance, during the course of further application, is no longer able to afterdiffuse into those regions of matrix (22) which are more distant from the deposit (23), once the originally contained active substance in the matrix has been released, due to the geometric conditions. As is shown by the corresponding in vivo-release profile according to FIG. 2b, the flux decreases to a substantially constant, lower value, after exceeding a certain maximum. Thus, in general, lower maintenance dosages are adjustable after an increased initial dosage.

Figure 3A:
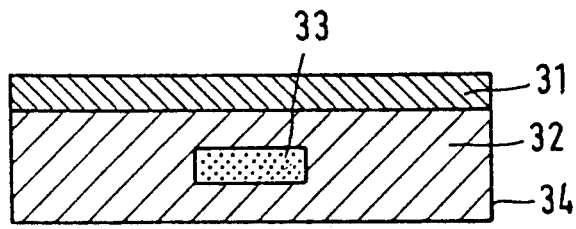
FIG. 3b shows a diagram of the in vivo-release profile of the plaster according to FIG. 3a, FIG. 4 shows a section through another preferred embodiment of the plaster according to the present invention.
Figure 3B:
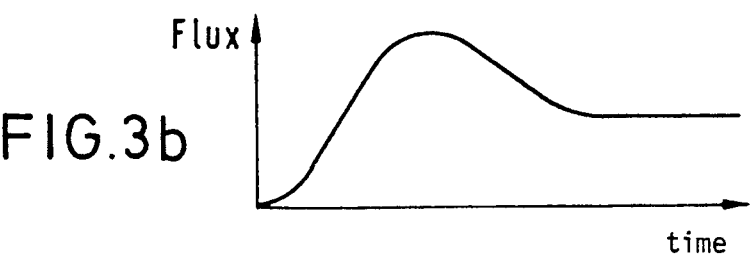

FIG. 3a shows a schematic section through a further embodiment of the plaster according to the present invention with backing layer (31), pressure-sensitive adhesive matrix (32), embedded deposit (33), and edge of matrix (34). In this figure the distance between deposit (33) and edge of matrix (34) is further extended compared to that of embodiment according to FIG. 2a so that even larger regions of the matrix (32) cannot be provided with active substance during application. However, since the total releasing surface is clearly larger than that shown in FIG. 2a, a higher initial maximum is obtained according to FIG. 3b, in which the corresponding flux is indicated, said initial flux, in the course of application then decreases to approximately the same value as that of FIG. 2b.

The deposit within the matrix may be positioned symmetrically or asymmetrically, whereby it must always be assured that the space between deposit and releasing surface can be bridged in the sense of an intended release by diffusion of the active substances. As a matter of fact, the desired release profile is of significant importance in this connection. The most favourable space can be calculated in some cases, or must experimentally be determined in many cases.

Figure 4:
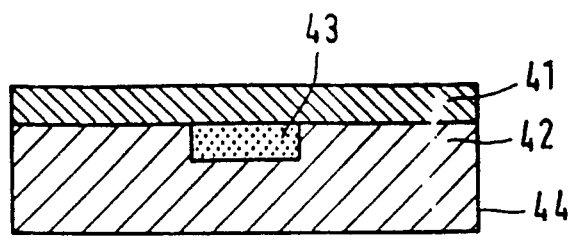

FIG. 4 represents a schematic section through another embodiment of the plaster according to the present invention. Here, the remarkable feature is the position of deposit (43) which is only partially embedded into the pressure-sensitive adhesive matrix (42) and contacts backing layer (41) at one side. The distance of deposit (43) to edge of matrix (44) corresponds to that shown in FIG. 3a, however, the larger distance between deposit (43) and releasing surface influences the choice of suitable active substances for this embodiment. This embodiment may have advantages from the production standpoint.

Figure 5:
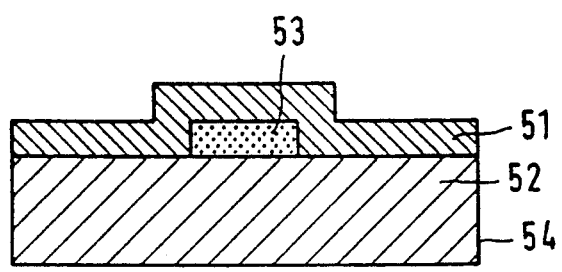
FIG. 5 shows a section through yet another preferred embodiment of the plaster according to the present invention.

As can be seen from FIG. 5, which represents a section through yet another embodiment of the plaster according to the present invention, deposit (53) may also be mounted on pressure-sensitive adhesive matrix (52), whereby for the rest it is surrounded by backing layer (51). The statements made for FIG. 4 apply to the space between deposit (53) and edge of matrix (54) and that between deposit and releasing surface. Here, too, advantages with respect to production may be decisive for choosing this embodiment.

Figure 6:
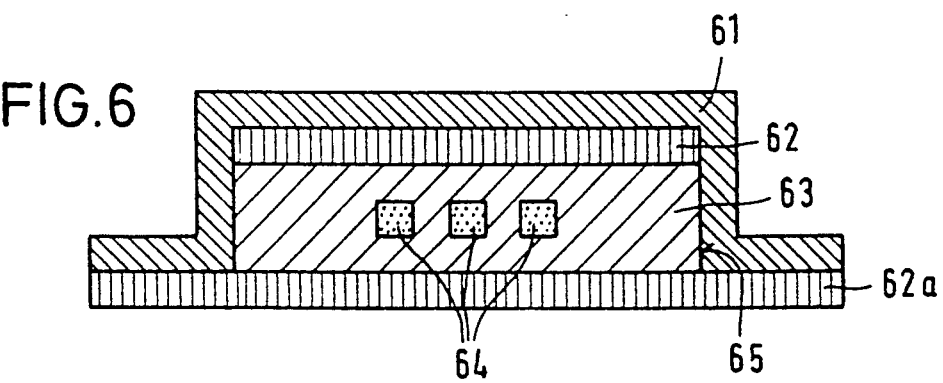
FIG. 6 shows a section through an embodiment of the plaster according to the present invention provided with several active substance deposits.

FIG. 6 schematically represents a section through an embodiment of the plaster according to the present invention in which three deposits (64) which are separated from each other are embedded in a non-adhesive matrix (63). Matrix (63) is connected with backing layer (61) via a pressure-sensitive adhesive intermediate layer (62), whereby backing layer (61) as well covers the edge (65) of the matrix, and builds an edge extending parallely to the skin. Fixing the plaster to the skin is effected by a pressure-sensitive adhesive layer (62a) which in permeable to the active substance and extends over the whole free surface of matrix (63) as well as over extending edges of backing layer (61).

The design of the plaster with several deposits points out another possibility to influence the release profile. The spacial isolation of deposit portions of the same total volume allows fresh delivery of active substances by diffusion into larger regions of the matrix, compared to a single deposit exhibiting the same volume. However, the condition according to the present invention with respect to the space of deposit to the plaster edge has to remain fulfilled. As a matter of fact, the space between at least two deposit members may be such large that it exceeds the possible diffusion path from the deposit part into the matrix during the application period of at least one active substance.

Figure 7:
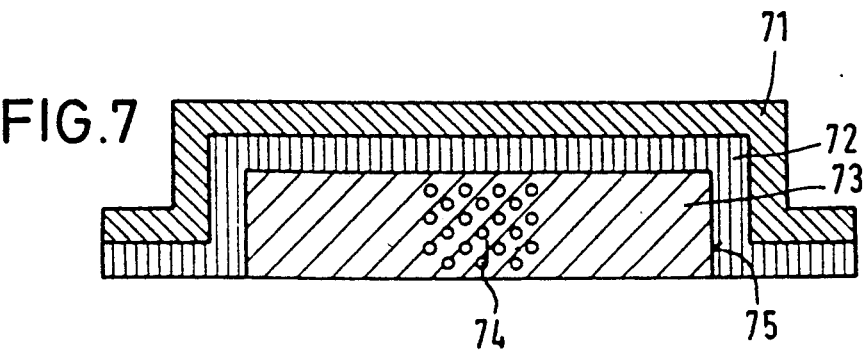
FIG. 7 shows a section through an embodiment of the plaster according to the present invention provided with a variety of active substance deposits.

FIG. 7 is an example with respect to the further division of the deposit. FIG. 7 represents a schematic section through a further embodiment of the plaster according to the present invention. The non-adhesive matrix (73) is interspersed with several small deposits (74) in its middle, whereby these deposits may be solid or flowable bodies or as well microcapsules. Matrix (73) is connected with backing layer (71), except for that surface facing the skin, via a pressure-sensitive adhesive layer (72); edge (75) of the matrix is covered, too. Pressure-sensitive adhesive layer (72) also spreads the extending edges of backing layer (71), thereby forming the fixing device to the skin, since that surface of matrix (73) which is in direct contact with the skin is non-adhesive.

For the sake of clarity, the protective layers for those surfaces facing the skin have not been drawn in all figures showing sections through plaster embodiments. As a matter of fact, they constitute an important component of the plasters according to the present invention. The dimension of the plasters may widely be varied with respect to outlines and sizes; in this connection, the therapeutic requirements as well as those determined by the site of application have to be considered principally, aspects concerning handling have to be considered, too.

It is understood that the specification and examples are illustrative but not limitative of the present invention and that other embodiments within the spirit and scope of the invention will suggest themselves to those skilled in the art.

I claim:

1. A plaster for the controlled release of active substance to the skin comprising
    a) a backing layer which is spaced from the skin, the backing layer comprising at least one material selected from the group consisting of polyethylene, polypropylene, polyester, polyamide, metal foil optionally coated with a polymeric substrate, textile fabric and polymer foil vapourized with metal,
    b) a matrix containing active substance in a first concentration, in use intended to contact the skin, the matrix comprising at least one polymeric material selected from the group consisting of rubber, a synthetic homo-, co- or block copolymer, a poly(-meth)acrylate or copolymer thereof, a polyurethane, a silicone, polyvinylpyrrolidone, ethyl cellulose, hydroxypropylcellulose, hydroxypropylmethylcellulosephthalate, polyvinyl alcohol or a copolymer thereof with vinyl laurate or maleic acid, vinyl acetate or a copolymer thereof with vinyl laurate or maleic acid, a polyvinyl ether, butyl rubber and polycaprolactam,
    c) a deposit containing active substance in a higher concentration than said first concentration, in use intended to be spaced from the skin, said deposit contacting the matrix of lower concentration, the deposit comprising a single or multiple layer inserted between a back side matrix layer and a matrix layer on the skin side, when multiple layers are present their thickness ratio falling in the range of 1:1 to 1:20,
    d) and adhesive for adhering the lower concentration matrix to the skin,
    the dimension and position of the active substance deposit in contact with the matrix being chosen in such manner that, at least in one direction, the space between deposit and a matrix edge, which contacts the releasing surface, is larger than the diffusion path from the deposit into the matrix during the course of application of at least one active substance.

2. The plaster according to claim 1, wherein at least one active substance deposit consists essentially of active substance or substances.

3. The plaster according to claim 1, wherein at least one active substance deposit comprises at least one inert auxiliary agent.

4. The plaster according to claim 1, wherein at least one active substance deposit is present in solid or flowable form.

5. The plaster according to claim 1, wherein it is built up at least partially in layers, as a laminate or at least partially in layers and as a laminate.

6. The plaster according to claim 5, wherein the matrix consists of at least two layers, whereby at least one active substance deposit is incorporated between a back-side matrix layer and a matrix layer facing the skin, and that the thickness ratio of the matrix layers is in the range of 1:1 to 1:20.

7. The plaster according to claim 6, wherein the matrix consists of at least two layers, whereby at least one active substance deposit is incorporated between a back-side matrix layer and a matrix layer facing the skin, and that the thickness ratio of the matrix layers is in the range of 1:1 to 1:5.

8. The plaster according to claim 5, wherein at least one active substance deposit is formed of at least one layer.

9. The plaster according to claim 1, wherein the matrix is pressure-sensitive adhesive.

10. The plaster according to claim 1, wherein the matrix or at least one matrix layer exhibits pressure-sensitive adhesive devices on at least one side.

11. The plaster according to claim 1, wherein pressure-sensitive adhesive portions embedded in the matrix form the fixing device.

12. The plaster according to claim 1, wherein at least one active substance deposit is positioned between matrix and backing layer.

13. The plaster according to claim 1, wherein it exhibits a removable protective layer for those surfaces facing the skin.

14. The plaster according to claim 1, wherein it comprises an amount of active substance amounting to up to 20 times the therapeutically required amount.

* * * * *